United States Patent [19]
Parrish et al.

[11] Patent Number: 5,814,510
[45] Date of Patent: Sep. 29, 1998

[54] ATTENUATED CANINE PARVOVIRUS VACCINE

[75] Inventors: Colin R. Parrish, Ithaca, N.Y.; Allen Gruenberg, Wellington, New Zealand; Leland E. Carmichael, Ithaca, N.Y.

[73] Assignee: Cornell Research Foundation, Inc., Ithaca, N.Y.

[21] Appl. No.: 336,345

[22] Filed: Nov. 8, 1994

[51] Int. Cl.$^6$ .............................. C12N 7/04; C12N 7/00; A61K 39/12; C07H 21/04
[52] U.S. Cl. ................... 435/236; 435/235.1; 424/186.1; 424/204.1; 536/23.72; 536/24.1
[58] Field of Search ............................. 424/186.1, 204.1; 435/235.1, 236; 536/23.72, 24.1

[56] References Cited

U.S. PATENT DOCUMENTS

| | | | |
|---|---|---|---|
| 4,193,990 | 3/1980 | Appel et al. | 424/89 |
| 4,193,991 | 3/1980 | Appel et al. | 424/89 |
| 4,303,645 | 12/1981 | Carmichael et al. | 424/89 |
| 4,810,494 | 3/1989 | Welsh | 424/89 |
| 4,971,793 | 11/1990 | Wood et al. | 424/88 |

OTHER PUBLICATIONS

Churchill, Preliminary development of a live attenuated canine parvovirus vaccine from an isolate of British origin, The Veterinary Record, 120:334–339, 1987.
Ausubel et al., 1989, Current Protocols in Molecular Biology, Greene Publishing Associates and Wiley Interscience, Chapter 8.
Chang et al., 1988, "Multiple amino acids in the capsid structure of canine parvovirus coordinately determine the canine host range and specific antigenic and hemagglutination properites", J Virol 66(12):6858–6867.
Mazzara et al., 1987, "Successful vaccination of dogs with empty capsids derived from canine parvovirus–bovine papillomavirus chimeric plasmids", Vaccines 87, Cold Spring Harbor Laboratory Press, pp. 419–424.
Botstein and Shortle, 1985, "Strategies and applications of in vitro mutagensis", Science 229:1193–1201.
Parrish et al., 1984, "Characterization of antigenic variation among mink enteritis virus isolates", Am J Vet Res 45:2591–2599.
Zoller and Smith, 1984, "Oligonucleotide–directed mutagenesis: A simple method using two oligonucleotide primers and a single stranded DNA template", DNA 3(6):479–488.
Carmichael et al., 1983, "A modified live canine parvovirus vaccine II. Immune Response", Cornell Vet 73:13–29.
Carmichael et al., 1981, "A modified live canine parvovirus strain with novel plaque characteristics I. Viral attenuation and dog response", Cornell Vet 71:408–427.
Carmichael et al., 1980, "Hemagglutination by canine parvovirus: Serologic studies and diagnostic applications", Am J Vet Res 41(5):784–791.
Appel et al., 1979, "Isolation and immunisation studies of a canine parvo–like virus from dogs with haemorrhagic enteritis", Vet Record 105:156–159.
Bovarnick et al., 1950, "The influence of certain salts, amino acids, sugars, and proteins on the stability of rickettsiae", J Bact 59:509–522.

(List continued on next page.)

*Primary Examiner*—Ponnathapura Achutamurthy
*Assistant Examiner*—Hankyel T. Park
*Attorney, Agent, or Firm*—Pennie & Edmonds LLP

[57] ABSTRACT

The invention is directed to a novel attenuated canine parvovirus (CPV) strain which may be used as a veterinary vaccine against CPV disease. The invention is further directed to a virus stock generated from a genomic DNA clone of the attenuated CPV strain which is used as a veterinary vaccine and is able to confer protective immunity to dogs against challenge with virulent CPV. Methods are given for the production of an attenuated CPV virus from a cloned CPV genome which may be used as a veterinary vaccine.

33 Claims, 8 Drawing Sheets

OTHER PUBLICATIONS

Gruenberg et al., 1993, "Preparation and analysis of a molecular clone of an atenuated strain of canine parvovirus" Abstract, 5th Parvovirus Workshop, Nov. 10–14, 1993, Crystal River, Florida.

Lopez de Turiso et al., 1992, "Recombinant vaccine for canine parvovirus in dogs", J. Virol 66(5)1748–2753.

Saliki et al., 1992, "Canine parvovirus empty capsids produced by expression in a baculovirus vector: Use in analsys of viral properties and immunization of dogs", J Gen Virol 73:369–374.

Parrish et al., 1991, "Mapping specific functions in the capsid structure of canine parvovirus and feline panleukopenia virus using infectious plasmid clones", Virology 183:195–205.

Parrish et al., 1991, "Rapid antigenic–type replacement and DNA sequence evolution of canine parvovirus", J Virol 65(12):6544–6552.

Parrish, 1990, "Emergence, natural history, and variation of canine, mink, and feline parvoviruses", Adv Virus Res 38:403–450.

```
ATCATTCTTT AGAACCAACT GACCAAGTTC ACGTACGTAT GACGTGATGA CGCGCGCTAC    60
GCCCGCTGCC TACGGCAGTC ACACGTCATA CGTACGTTCC TTGGTCAGTT GGTTCTAAAG   120
AATGATAGGC GGTTTGTGTG TTTAAACTTG GGCGGGAAAA GGTGGCGGGC TAATTGTGGG   180
CGTGGTTAAA GGTATAAAAG ACAAACCATA GACCGTTACT GACATTCGCT TCTTGTCTTT   240
GACAGAGTGA ACCTCTCTTA CTTTGACTAA CCATGTCTGG CAACCAGTAT ACTGAGGAAG   300
TTATGGAGGG AGTAAATTGG TTAAAGAAAC ATGCAGAAAA TGAAGCATTT TCGTTTGTTT   360
TTAAATGTGA CAACGTCCAA CTAAATGGAA AGGATGTTCG CTGGAACAAC TATACCAAAC   420
CAATTCAAAA TGAAGAGCTA ACATCTTTAA TTAGAGGAGC ACAAACAGCA ATGGATCAAA   480
CCGAAGAAGA AGAAATGGAC TGGGAATCGG AAGTTGATAG TCTCGCCAAA AAGCAAGTAC   540
AAACTTTTGA TGCATTAATT AAAAAATGTC TTTTTGAAGT CTTTGTTTCT AAAAATATAG   600
AACCAAATGA ATGTGTTTGG TTTATTCAAC ATGAATGGGG AAAAGATCAA GGCTGGCATT   660
GTCATGTTTT ACTTCATAGT AAGAACTTAC AACAAGCAAC TGGTAAATGG CTACGCAGAC   720
AAATGAATAT GTATTGGAGT AGATGGTTGG TGACTCTTTG TTCGGTAAAC TTAACACCAA   780
CTGAAAAGAT TAAGCTCAGA GAAATTGCAG AAGATAGTGA ATGGGTGACT ATATTAACAT   840
ACAGACATAA GCAAACAAAA AAAGACTATG TTAAAATGGT TCATTTTGGA AATATGATAG   900
CATATTACTT TTTAACAAAG AAAAAAATTG TCCACATGAC AAAAGAAAGT GGCTATTTTT   960
TAAGTACTGA TTCTGGTTGG AAATTTAACT TTATGAAGTA TCAAGACAGA CAAATTGTCA  1020
GCACACTTTA CACTGAACAA ATGAAACCAG AAACCGTTGA AACCACAGTG ACGACAGCAC  1080
AGGAAACAAA GCGCGGGAGA ATTCAAACTA AAAAGGAAGT GTCAATCAAA TGTACTTTGC  1140
GGGACTTGGT TAGTAAAAGA GTAACATCAC CTGAAGACTG GATGATGTTA CAACCAGATA  1200
GTTATATTGA AATGATGGCA CAACCAGGAG GTGAAAATCT TTTAAAAAAT ACACTTGAAA  1260
TTTGTACTTT GACTTTAGCA AGAACAAAAA CAGCATTTGA ATTAATACTT GAAAAAGCAG  1320
ATAATACTAA ACTAACTAAC TTTGATCTTG CAAATTCTAG AACATGTCAA ATTTTTAGAA  1380
TGCACGGATG GAATTGGATT AAAGTTTGTC ACGCTATAGC ATGTGTTTTA AATAGACAAG  1440
GTGGTAAAAG AAATACAGTT CTTTTCATG GACCAGCAAG TACAGGAAAA TCTATCATTG  1500
CTCAAGCCAT AGCACAAGCT GTGGGTAATG TTGGTTGTTA TAATGCAGCA AATGTAAATT  1560
TTCCATTTAA TGACTGTACC AATAAAAATT TAATTTGGAT TGAAGAAGCT GGTAACTTTG  1620
GTCAACAAGT TAATCAATTT AAAGCAATCT GTTCTGGACA AACAATTAGA ATTGATCAAA  1680
AAGGTAAAGG AAGTAAGCAA ATTGAACCAA CTCCAGTAAT TATGACAACT AATGAAAATA  1740
TAACAATTGT GAGAATTGGA TGTGAAGAAA GACCTGAACA TACACAACCA ATAAGAGACA  1800
GAATGTTGAA CATTAAGTTA GTATGTAAGC TTCCAGGAGA CTTTGGTTTG GTTGATAAAG  1860
AAGAATGGCC TTTAATATGT GCATGGTTAG TTAAACATGG TTTTGAATCA ACCATGGCTA  1920
ACTATACACA TCATTGGGGA AAAGTACCAG AATGGGATGA AAACTGGGCG GAGCCTAAAA  1980
```

FIG.3A

```
TACAAGAAGG TATAAATTCA CCAGGTTGCA AAGACTTAGA GACACAAGCG GCAAGCAATC   2040
CTCAGAGTCA AGACCAAGTT CTAACTCCTC TGACTCCGGA CGTAGTGGAC CTTGCACTGG   2100
AACCGTGGAG TACTCCAGAT ACGCCTATTG CAGAAACTGC AAATCAACAA TCAAACCAAC   2160
TTGGCGTTAC TCACAAAGAC GTGCAAGCGA GTCCGACGTG GTCCGAAATA GAGGCAGACC   2220
TGAGAGCCAT CTTTACTTCT GAACAATTGG AAGAAGATTT TCGAGACGAC TTGGATTAAG   2280
GTACGATGGC ACCTCCGGCA AAGAGAGCCA GGAGAGGTAA GGGTGTGTTA GTAAAGTGGG   2340
GGGAGGGGAA AGATTTAATA ACTTAACTAA GTATGTGTTT TTTTATAGGA CTTGTGCCTC   2400
CAGGTTATAA ATATCTTGGG CCTGGGAACA GTCTTGACCA AGGAGAACCA ACTAACCCTT   2460
CTGACGCCGC TGCAAAAGAA CACGACGAAG CTTACGCTGC TTATCTTCGC TCTGGTAAAA   2520
ACCCATACTT ATATTTCTCG CCAGCAGATC AACGCTTTAT AGATCAAACT AAGGACGCTA   2580
AAGATTGGGG GGGGAAAATA GGACATTATT TTTTAGAGC TAAAAGGCA ATTGCTCCAG    2640
TATTAACTGA TACACCAGAT CATCCATCAA CATCAAGACC AACAAAACCA ACTAAAAGAA   2700
GTAAACCACC ACCTCATATT TTCATCAATC TTGCAAAAAA AAAAAAAGCC GGTGCAGGAC   2760
AAGTAAAAAG AGACAATCTT GCACCAATGA GTGATGGAGC AGTTCAACCA GACGGTGGTC   2820
AACCTGCTGT CAGAAATGAA AGAGCTACAG GATCTGGGAA CGGGTCTGGA GGCGGGGGTG   2880
GTGGTGGTTC TGGGGGTGTG GGGATTTCTA CGGGTACTTT CAATAATCAG ACGGAATTTA   2940
AATTTTTGGA AAACGGATGG GTGGAAATCA CAGCAAACTC AAGCAGACTT GTACATTTAA   3000
ATATGCCAGA AAGTGAAAAT TATAGAAGAG TGGTTGTAAA TAATTTGGAT AAAACTGCAG   3060
TTAACGGAAA CATGGCTTTA GATGATACTC ATGCACAAAT TGTAACACCT TGGTCATTGG   3120
TTGATGCAAA TGCTTGGGGA GTTTGGTTTA ATCCAGGAGA TTGGCAACTA ATTGTTAATA   3180
CTATGAGTGA GTTGCATTTA GTTAGTTTTG AACAAGAAAT TTTTAATGTT GTTTTAAAGA   3240
CTGTTTCAGA ATCTGCTACT CAGCCACCAA CTAAAGTTTA TAATAATGAT TTAACTGCAT   3300
CATTGATGGT TGCATTAGAT AGTAATAATA CTATGCCATT TACTCCAGCA GCTATGAGAT   3360
CTGAGACATT GGGTTTTTAT CCATGGAAAC CAACCATACC AACTCCATGG AGATATTATT   3420
TTCAATGGGA TAGAACATTA ATACCATCTC ATACTGGAAC TAGTGGCACA CCAACAAATA   3480
TATACCATGG TACAGATCCA GATGATGTTC AATTTTATAC TATTGAAAAT TCTGTGCCAG   3540
TACACTTACT AAGAACAGGT GATGAATTTG CTACAGGAAC ATTTTTTTTT GATTGTAAAC   3600
CATGTAGACT AACACATACA TGGCAAACAA ATAGAGCATT GGGCTTACCA CCATTTCTAA   3660
ATTCTTTGCC TCAATCTGAA GGAGGTACTA ACTTTGGTTA TATAGGAGTT CAACAAGATA   3720
AAAGACGTGG TGTAACTCAA ATGGGAAATA CAAACTATAT TACTGAAGCT ACTATTATGA   3780
GACCAGCTGA GGTTGGTTAT AGTGCACCAT ATTATTCTTT TGAGGCGTCT ACACAAGGGC   3840
CATTTAAAAC ACCTATTGCA GCAGGACGGG GGGAGCGCA AACAGATGAA AATCAAGCAG    3900
CAGATGGTGA TCCAAGATAT GCATTTGGTA GACAACATGG TCAAAAAACT ACCACAACAG   3960
GAGAAACACC TGAGAGATTT ACATATATAG CACATCAAGA TACAGGAAGA TATCCAGAAG   4020
```

FIG.3B

```
GAGATTGGAT TCAAAATATT AACTTTAACC TTCCTGTAAC AGATGATAAT GTATTGCTAC    4080
CAACAGATCC AATTGGAGGT AAAACAGGAA TTAACTATAC TAATATATTT AATACTTATG    4140
GTCCTTTAAC TGCATTAAAT AATGTACCAC CAGTTTATCC AAATGGTCAA ATTTGGGATA    4200
AAGAATTTGA TACTGACTTA AAACCAAGAC TTCATGTAAA TGCACCATTT GTTTGTCAAA    4260
ATAATTGTCC TGGTCAATTA TTTGTAAAAG TTGCGCCTAA TTTAACAAAT GAATATGATC    4320
CTGATGCATC TGCTAATATG TCAAGAATTG TAACTTACTC AGATTTTTGG TGGAAAGGTA    4380
AATTAGTATT TAAAGCTAAA CTAAGAGCCT CTCATACTTG GAATCCAATT CAACAAATGA    4440
GTATTAATGT AGATAACCAA TTTAACTATG TACCAAGTAA TATTGGAGGT ATGAAAATTG    4500
TATATGAAAA ATCTCAACTA GCACCTAGAA AATTATATTA ACATACTTAC TATGTTTTTA    4560
TGTTTATTAC ATATCAACTA GCACCTAGAA AATTATATTA ATATACTTAC TATGTTTTTA    4620
TGTTTATTAC ATATTATTTT AAGATTAATT AAATTACAGC ATAGAAATAT TGTACTTGTA    4680
TTTGATATAG GATTTAGAAG GTTTGTTATA TGGTATACAA TAACTGTAAG AAATAGAAGA    4740
ACATCTAGAT CATAGTTAGT AGTTTGTTTT ATAAAATGTA TTGTAAACCA TTAATGTATG    4800
TTGTTATGGT GTGGGTGGTT GGTTGGTTTG CCCTTAGAAT ATGTTAAGGA CCAAAAAAAA    4860
TCAATAAAAG ACATTTAAAA TTAAATGGCC TCGTATACTG TCTATAAGGT GAACTAACCT    4920
TACCATAAGT ATCAATCTGT CTTTAAGGGG GGGGTGGGTG GGAGATGCAC AACATCAGTA    4980
GACTGACTGG CCTGGTTGGT TGCTCTGCTT AATCAACCAG ACCGCGTAGC GGTCTGGTTG    5040
ATTAAGCGC                                                           5049
```

FIG.3C

```
ATCATTCTTT AGAACCAACT GACCAAGTTC ACGTACGTAT GACGTGATGA CGCGCGCTGC    60
GCGCGCTGCC TACGGCAGTC ACACGTCATA CGTACGCTCC TTGGTCAGTT GGTTCTAAAG   120
AATGATAGGC GGTTTGTGTG TTTAAACTTG GGCGGGAAAA GGTGGCGGGC TAATTGTGGG   180
CGTGGTTAAA GGTATAAAAG ACAAACCATA GACCGTTACT GACATTCGCT TCTTGTCTTT   240
GACAGAGTGA ACCTCTCTTA CTTTGACTAA CCATGTCTGG CAACCAGTAT ACTGAGGAAG   300
TTATGGAGGG AGTAAATTGG TTAAAGAAAC ATGCAGAAAA TGAAGCATTT TCGTTTGTTT   360
TTAAATGTGA CAACGTCCAA CTAAATGAAA AGGATGTTCG CTGGAACAAC TATACCAAAC   420
CAATTCAAAA TGAAGAGCTA ACATCTTTAA TTAGAGGAGC ACAAACAGCA ATGGATCAAA   480
CCGAAGAAGA AGAAATGGAC TGGGAATCGG AAGTTGATAG TCTCGCCAAA AAGCAAGTAC   540
AAACTTTTGA TGCATTAATT AAAAAAATGTC TTTTTGAAGT CTTTGTTTCT AAAAATATAG   600
AACCAAATGA ATGTGTTTGG TTTATTCAAC ATGAATGGGG AAAAGATCAA GGCTGGCATT   660
GTCATGTTTT ACTTCATAGT AAGAACTTAC AACAAGCAAC TGGTAAATGG CTACGCAGAC   720
AAATGAATAT GTATTGGAGT AGATGGTTGG TGACTCTTTG TTCGGTAAAC TTAACACCAA   780
CTGAAAAGAT TAAGCTCAGA GAAATTGCAG AAGATAGTGA ATGGGTGACT ATATTAACAT   840
ACAGACATAA GCAAACAAAA AAAGACTATG TTAAAATGGT TCATTTTGGA AATATGATAG   900
CATATTACTT TTTAACAAAG AAAAAAATTG TCCACATGAC AAAAGAAAGT GGCTATTTTT   960
TAAGTACTGA TTCTGGTTGG AAATTTAACT TTATGAAGTA TCAAGACAGA CAAATTGTCA  1020
GCACACTTTA CACTGAACAA ATGAAACCAG AAACCGTTGA AACCACAGTG ACGACAGCAC  1080
AGGAAACAAA GCGCGGGAGA ATTCAAACTA AAAGGAAGT GTCAATCAAA TGTACTTTGC   1140
GGGACTTGGT TAGTAAAAGA GTAACATCAC CTGAAGACTG GATGATGTTA CAACCAGATA  1200
GTTATATTGA AATGATGGCA CAACCAGGAG GTGAAAATCT TTTAAAAAAT ACACTTGAAA  1260
TTTGTACTTT GACTTTAGCA AGAACAAAAA CAGCATTTGA ATTAATACTT GAAAAAGCAG  1320
ATAATACTAA ACTAACTAAC TTTGATCTTG CAAATTCTAG AACATGTCAA ATTTTTAGAA  1380
TGCACGGATG GAATTGGATT AAAGTTTGTC ACGCTATAGC ATGTGTTTTA AATAGACAAG  1440
GTGGTAAAAG AAATACAGTT CTTTTCATG GACCAGCAAG TACAGGAAAA TCTATCATTG   1500
CTCAAGCCAT AGCACAAGCT GTGGGTAATG TTGGTTGTTA TAATGCAGCA AATGTAAATT  1560
TTCCATTTAA TGACTGTACC AATAAAAATT TAATTTGGAT TGAAGAAGCT GGTAACTTTG  1620
GTCAACAAGT TAATCAATTT AAAGCAATCT GTTCTGGACA AACAATTAGA ATTGATCAAA  1680
AAGGTAAAGG AAGTAAGCAA ATTGAACCAA CTCCAGTAAT TATGACAACT AATGAAAATA  1740
TAACAATTGT GAGAATTGGA TGTGAAGAAA GACCTGAACA TACACAACCA ATAAGAGACA  1800
GAATGTTGAA CATTAAGTTA GTATGTAAGC TTCCAGGAGA CTTTGGTTTG GTTGATAAAG  1860
AAGAATGGCC TTTAATATGT GCATGGTTAG TTAAACATGG TTTTGAATCA ACCATGGCTA  1920
```

FIG.4A

```
ACTATACACA TCATTGGGGA AAAGTACCAG AATGGGATGA AAACTGGGCG GAGCCTAAAA    1980
TACAAGAAGG TATAAATTCA CCAGGTTGCA AAGACTTAGA GACACAAGCG GCAAGCAATC    2040
CTCAGAGTCA AGACCAAGTT CTAACTCCTC TGACTCCGGA CGTAGTGGAC CTTGCACTGG    2100
AACCGTGGAG TACTCCAGAT ACGCCTATTG CAGAAACTGC AAATCAACAA TCAAACCAAC    2160
TTGGCGTTAC TCACAAAGAC GTGCAAGCGA GTCCGACGTG GTCCGAAATA GAGGCAGACC    2220
TGAGAGCCAT CTTTACTTCT GAACAATTGG AAGAAGATTT TCGAGACGAC TTGGATTAAG    2280
GTACGATGGC ACCTCCGGCA AAGAGAGCCA GGAGAGGTAA GGGTGTGTTA GTAAAGTGGG    2340
GGGAGGGGAA AGATTTAATA ACTTAACTAA GTATGTGTTT TTTTATAGGA CTTGTGCCTC    2400
CAGGTTATAA ATATCTTGGG CCTGGGAACA GTCTTGACCA AGGAGAACCA ACTAACCCTT    2460
CTGACGCCGC TGCAAAAGAA CACGACGAAG CTTACGCTGC TTATCTTCGC TCTGGTAAAA    2520
ACCCATACTT ATATTTCTCG CCAGCAGATC AACGCTTTAT AGATCAAACT AAGGACGCTA    2580
AAGATTGGGG GGGGAAAATA GGACATTATT TTTTAGAGCC TAAAAAGGCA ATTGCTCCAG    2640
TATTAACTGA TACACCAGAT CATCCATCAA CATCAAGACC AACAAAACCA ACTAAAAGAA    2700
GTAAACCACC ACCTCATATT TTCATCAATC TTGCAAAAAA AAAAAAAGCC GGTGCAGGAC    2760
AAGTAAAAAG AGACAATCTT GCACCAATGA GTGATGGAGC AGTTCAACCA GACGGTGGTC    2820
AACCTGCTGT CAGAAATGAA AGAGCTACAG GATCTGGGAA CGGGTCTGGA GGCGGGGGTG    2880
GTGGTGGTTC TGGGGGTGTG GGGATTCTA CGGGTACTTT CAATAATCAG ACGGAATTTA    2940
AATTTTTGGA AAACGGATGG GTGGAAATCA CAGCAAACTC AAGCAGACTT GTACATTTAA    3000
ATATGCCAGA AAGTGAAAAT TATAGAAGAG TGGTTGTAAA TAATTTGGAT AAAACTGCAG    3060
TTAACGGAAA CATGGCTTTA GATGATACTC ATGCACAAAT TGTAACACCT TGGTCATTGG    3120
TTGATGCAAA TGCTTGGGGA GTTTGGTTTA ATCCAGGAGA TTGGCAACTA ATTGTTAATA    3180
CTATGAGTGA GTTGCATTTA GTTAGTTTTG AACAAGAAAT TTTAATGTT GTTTTAAAGA     3240
CTGTTTCAGA ATCTGCTACT CAGCCACCAA CTAAAGTTTA TAATAATGAT TTAACTGCAT    3300
CATTGATGGT TGCATTAGAT AGTAATAATA CTATGCCATT TACTCCAGCA GCTATGAGAT    3360
CTGAGACATT GGGTTTTTAT CCATGGAAAC CAACCATACC AACTCCATGG AGATATTATT    3420
TTCAATGGGA TAGAACATTA ATACCATCTC ATACTGGAAC TAGTGGCACA CCAACAAATA    3480
TATACCATGG TACAGATCCA GATGATGTTC AATTTTATAC TATTGAAAAT TCTGTGCCAG    3540
TACACTTACT AAGAACAGGT GATGAATTTG CTACAGGAAC ATTTTTTTTT GATTGTAAAC    3600
CATGTAGACT AACACATACA TGGCAAACAA ATAGAGCATT GGGCTTACCA CCATTTCTAA    3660
ATTCTTTGCC TCAATCTGAA GGAGGTACTA ACTTTGGTTA TATAGGAGTT CAACAAGATA    3720
AAAGACGTGG TGTAACTCAA ATGGGAAATA CAAACTATAT TACTGAAGCT ACTATTATGA    3780
GACCAGCTGA GGTTGGTTAT AGTGCACCAT ATTATTCTTT TGAGGCGTCT ACACAAGGGC    3840
CATTTAAAAC ACCTATTGCA GCAGGACGGG GGGGAGCGCA AACAGATGAA AATCAAGCAG    3900
CAGATGGTGA TCCAAGATAT GCATTTGGTA GACAACATGG TCAAAAAACT ACCACAACAG    3960
```

FIG.4B

```
GAGAAACACC TGAGAGATTT ACATATATAG CACATCAAGA TACAGGAAGA TATCCAGAAG    4020
GAGATTGGAT TCAAAATATT AACTTTAACC TTCCTGTAAC AGATGATAAT GTATTGCTAC    4080
CAACAGATCC AATTGGAGGT AAAACAGGAA TTAACTATAC TAATATATTT AATACTTATG    4140
GTCCTTTAAC TGCATTAAAT AATGTACCAC CAGTTTATCC AAATGGTCAA ATTTGGGATA    4200
AAGAATTTGA TACTGACTTA AAACCAAGAC TTCATGTAAA TGCACCATTT GTTTGTCAAA    4260
ATAATTGTCC TGGTCAATTA TTTGTAAAAG TTGCGCCTAA TTTAACAAAT GAATATGATC    4320
CTGATGCATC TGCTAATATG TCAAGAATTG TAACTTACTC AGATTTTTGG TGGAAAGGTA    4380
AATTAGTATT TAAAGCTAAA CTAAGAGCCT CTCATACTTG GAATCCAATT CAACAAATGA    4440
GTATTAATGT AGATAACCAA TTTAACTATG TACCAAGTAA TATTGGAGGT ATGAAAATTG    4500
TATATGAAAA ATCTCAACTA GCACCTAGAA AATTATATTA ACATACTTAC TATGTTTTTA    4560
TGTTTATTAC ATATCAACTA GCACCTAGAA AATTATATTA ATATACTTAC TATGTTTTTA    4620
TGTTTATTAC ATATTATTTT AAGATTAATT AAATTACAGC ATAGAAATAT TGTACTTGTA    4680
TTTGATATAG GATTTAGAAG GTTTGTTATA TGGTATACAA TAACTGTAAG AAATAGAAGA    4740
ACATTTAGAT CATAGTTAGT AGTTTGTTTT ATAAAATGTA TTGTAAACCA TTAATGTATG    4800
TTGTTATGGT GTGGGTGGTT GGTTGGTTTG CCCTTAGAAT ATGTTAAGGA CCAAAAAAAA    4860
TCAATAAAAG ACATTTAAAA CTAAATGGCC TCGTATACTG TCTATAAGGT GAACTAACCT    4920
TACCATAAGT ATCAATCTGT CTTTAAGGGG GGGGTGGGTG GGAGATGCAC AACATCAGTA    4980
GACTGACTGG CCTGGTTGGT TGCTCTGCTT AATCAACCAG ACCGCGTAGC GGTCTGGTTG    5040
ATTAAGCGC                                                           5049
```

FIG.4C

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5049 base pairs
        ( B ) TYPE: nucleic acid
        ( C ) STRANDEDNESS: both
        ( D ) TOPOLOGY: unknown ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Parvovirus ( x i ) SEQUENCE DESCRIPTION: SEQ ID NO:1:

```
ATCATTCTTT AGAACCAACT GACCAAGTTC ACGTACGTAT GACGTGATGA CGCGCGCTAC   60
GCGCGCTGCC TACGGCAGTC ACACGTCATA CGTACGTTCC TTGGTCAGTT GGTTCTAAAG  120
AATGATAGGC GGTTTGTGTG TTTAAACTTG GGCGGGAAAA GGTGGCGGGC TAATTGTGGG  180
CGTGGTTAAA GGTATAAAAG ACAAACCATA GACCGTTACT GACATTCGCT TCTTGTCTTT  240
GACAGAGTGA ACCTCTCTTA CTTTGACTAA CCATGTCTGG CAACCAGTAT ACTGAGGAAG  300
TTATGGAGGG AGTAAATTGG TTAAAGAAAC ATGCAGAAAA TGAAGCATTT TCGTTTGTTT  360
TTAAATGTGA CAACGTCCAA CTAAATGGAA AGGATGTTCG CTGGAACAAC TATACCAAAC  420
CAATTCAAAA TGAAGAGCTA ACATCTTTAA TTAGAGGAGC ACAAACAGCA ATGGATCAAA  480
CCGAAGAAGA AGAAATGGAC TGGGAATCGG AAGTTGATAG TCTCGCCAAA AAGCAAGTAC  540
AAACTTTTGA TGCATTAATT AAAAAATGTC TTTTTGAAGT CTTTGTTTCT AAAAATATAG  600
AACCAAATGA ATGTGTTTGG TTTATTCAAC ATGAATGGGG AAAAGATCAA GGCTGGCATT  660
GTCATGTTTT ACTTCATAGT AAGAACTTAC AACAAGCAAC TGGTAAATGG CTACGCAGAC  720
AAATGAATAT GTATTGGAGT AGATGGTTGG TGACTCTTTG TTCGGTAAAC TTAACACCAA  780
CTGAAAAGAT TAAGCTCAGA GAAATTGCAG AAGATAGTGA ATGGGTGACT ATATTAACAT  840
ACAGACATAA GCAAACAAAA AAAGACTATG TTAAAATGGT TCATTTTGGA AATATGATAG  900
CATATTACTT TTTAACAAAG AAAAAAATTG TCCACATGAC AAAAGAAAGT GGCTATTTTT  960
TAAGTACTGA TTCTGGTTGG AAATTTAACT TTATGAAGTA TCAAGACAGA CAAATTGTCA 1020
GCACACTTTA CACTGAACAA ATGAAACCAG AAACCGTTGA AACCACAGTG ACGACAGCAC 1080
AGGAAACAAA GCGCGGGAGA ATTCAAACTA AAAAGGAAGT GTCAATCAAA TGTACTTTGC 1140
GGGACTTGGT TAGTAAAAGA GTAACATCAC CTGAAGACTG GATGATGTTA CAACCAGATA 1200
GTTATATTGA AATGATGGCA CAACCAGGAG GTGAAAATCT TTTAAAAAAT ACACTTGAAA 1260
TTTGTACTTT GACTTTAGCA AGAACAAAAA CAGCATTTGA ATTAATACTT GAAAAAGCAG 1320
ATAATACTAA ACTAACTAAC TTTGATCTTG CAAATTCTAG AACATGTCAA ATTTTTAGAA 1380
TGCACGGATG GAATTGGATT AAAGTTTGTC ACGCTATAGC ATGTGTTTTA AATAGACAAG 1440
GTGGTAAAAG AAATACAGTT CTTTTTCATG GACCAGCAAG TACAGGAAAA TCTATCATTG 1500
CTCAAGCCAT AGCACAAGCT GTGGGTAATG TTGGTTGTTA TAATGCAGCA AATGTAAATT 1560
TTCCATTTAA TGACTGTACC AATAAAAATT TAATTTGGAT TGAAGAAGCT GGTAACTTTG 1620
GTCAACAAGT TAATCAATTT AAAGCAATCT GTTCTGGACA AACAATTAGA ATTGATCAAA 1680
AAGGTAAAGG AAGTAAGCAA ATTGAACCAA CTCCAGTAAT TATGACAACT AATGAAAATA 1740
TAACAATTGT GAGAATTGGA TGTGAAGAAA GACCTGAACA TACACAACCA ATAAGAGACA 1800
GAATGTTGAA CATTAAGTTA GTATGTAAGC TTCCAGGAGA CTTTGGTTTG GTTGATAAAG 1860
AAGAATGGCC TTTAATATGT GCATGGTTAG TTAAACATGG TTTTGAATCA ACCATGGCTA 1920
ACTATACACA TCATTGGGGA AAAGTACCAG AATGGGATGA AAACTGGGCG GAGCCTAAAA 1980
TACAAGAAGG TATAAATTCA CCAGGTTGCA AAGACTTAGA GACACAAGCG GCAAGCAATC 2040
CTCAGAGTCA AGACCAAGTT CTAACTCCTC TGACTCCGGA CGTAGTGGAC CTTGCACTGG 2100
```

| | | | | | | |
|---|---|---|---|---|---|---|
| AACCGTGGAG | TACTCCAGAT | ACGCCTATTG | CAGAAACTGC | AAATCAACAA | TCAAACCAAC | 2160 |
| TTGGCGTTAC | TCACAAAGAC | GTGCAAGCGA | GTCCGACGTG | GTCCGAAATA | GAGGCAGACC | 2220 |
| TGAGAGCCAT | CTTTACTTCT | GAACAATTGG | AAGAAGATTT | TCGAGACGAC | TTGGATTAAG | 2280 |
| GTACGATGGC | ACCTCCGGCA | AAGAGAGCCA | GGAGAGGTAA | GGGTGTGTTA | GTAAAGTGGG | 2340 |
| GGGAGGGGAA | AGATTTAATA | ACTTAACTAA | GTATGTGTTT | TTTTATAGGA | CTTGTGCCTC | 2400 |
| CAGGTTATAA | ATATCTTGGG | CCTGGGAACA | GTCTTGACCA | AGGAGAACCA | ACTAACCCTT | 2460 |
| CTGACGCCGC | TGCAAAAGAA | CACGACGAAG | CTTACGCTGC | TTATCTTCGC | TCTGGTAAAA | 2520 |
| ACCCATACTT | ATATTTCTCG | CCAGCAGATC | AACGCTTTAT | AGATCAAACT | AAGGACGCTA | 2580 |
| AAGATTGGGG | GGGGAAAATA | GGACATTATT | TTTTAGAGC | TAAAAGGCA | ATTGCTCCAG | 2640 |
| TATTAACTGA | TACACCAGAT | CATCCATCAA | CATCAAGACC | AACAAACCA | ACTAAAGAA | 2700 |
| GTAAACCACC | ACCTCATATT | TTCATCAATC | TTGCAAAAAA | AAAAAAAGCC | GGTGCAGGAC | 2760 |
| AAGTAAAAAG | AGACAATCTT | GCACCAATGA | GTGATGGAGC | AGTTCAACCA | GACGGTGGTC | 2820 |
| AACCTGCTGT | CAGAAATGAA | AGAGCTACAG | GATCTGGGAA | CGGGTCTGGA | GGCGGGGGTG | 2880 |
| GTGGTGGTTC | TGGGGGTGTG | GGGATTTCTA | CGGGTACTTT | CAATAATCAG | ACGGAATTTA | 2940 |
| AATTTTTGGA | AAACGGATGG | GTGGAAATCA | CAGCAAACTC | AAGCAGACTT | GTACATTTAA | 3000 |
| ATATGCCAGA | AAGTGAAAAT | TATAGAAGAG | TGGTTGTAAA | TAATTTGGAT | AAAACTGCAG | 3060 |
| TTAACGGAAA | CATGGCTTTA | GATGATACTC | ATGCACAAAT | TGTAACACCT | TGGTCATTGG | 3120 |
| TTGATGCAAA | TGCTTGGGGA | GTTTGGTTTA | ATCCAGGAGA | TTGGCAACTA | ATTGTTAATA | 3180 |
| CTATGAGTGA | GTTGCATTTA | GTTAGTTTTG | AACAAGAAAT | TTTTAATGTT | GTTTTAAAGA | 3240 |
| CTGTTTCAGA | ATCTGCTACT | CAGCCACCAA | CTAAAGTTTA | TAATAATGAT | TTAACTGCAT | 3300 |
| CATTGATGGT | TGCATTAGAT | AGTAATAATA | CTATGCCATT | TACTCCAGCA | GCTATGAGAT | 3360 |
| CTGAGACATT | GGGTTTTTAT | CCATGGAAAC | CAACCATACC | AACTCCATGG | AGATATTATT | 3420 |
| TTCAATGGGA | TAGAACATTA | ATACCATCTC | ATACTGGAAC | TAGTGGCACA | CCAACAAATA | 3480 |
| TATACCATGG | TACAGATCCA | GATGATGTTC | AATTTTATAC | TATTGAAAAT | TCTGTGCCAG | 3540 |
| TACACTTACT | AAGAACAGGT | GATGAATTTG | CTACAGGAAC | ATTTTTTTT | GATTGTAAAC | 3600 |
| CATGTAGACT | AACACATACA | TGGCAAACAA | ATAGAGCATT | GGGCTTACCA | CCATTTCTAA | 3660 |
| ATTCTTTGCC | TCAATCTGAA | GGAGGTACTA | ACTTTGGTTA | TATAGGAGTT | CAACAAGATA | 3720 |
| AAAGACGTGG | TGTAACTCAA | ATGGGAAATA | CAAACTATAT | TACTGAAGCT | ACTATTATGA | 3780 |
| GACCAGCTGA | GGTTGGTTAT | AGTGCACCAT | ATTATTCTTT | TGAGGCGTCT | ACACAAGGGC | 3840 |
| CATTAAAAAC | ACCTATTGCA | GCAGGACGGG | GGGGAGCGCA | AACAGATGAA | AATCAAGCAG | 3900 |
| CAGATGGTGA | TCCAAGATAT | GCATTTGGTA | GACAACATGG | TCAAAAAACT | ACCACAACAG | 3960 |
| GAGAAACACC | TGAGAGATTT | ACATATATAG | CACATCAAGA | TACAGGAAGA | TATCCAGAAG | 4020 |
| GAGATTGGAT | TCAAAATATT | AACTTTAACC | TTCCTGTAAC | AGATGATAAT | GTATTGCTAC | 4080 |
| CAACAGATCC | AATTGGAGGT | AAAACAGGAA | TTAACTATAC | TAATATATTT | AATACTTATG | 4140 |
| GTCCTTTAAC | TGCATTAAAT | AATGTACCAC | CAGTTTATCC | AAATGGTCAA | ATTTGGGATA | 4200 |
| AAGAATTTGA | TACTGACTTA | AAACCAAGAC | TTCATGTAAA | TGCACCATTT | GTTTGTCAAA | 4260 |
| ATAATTGTCC | TGGTCAATTA | TTTGTAAAAG | TTGCGCCTAA | TTTAACAAAT | GAATATGATC | 4320 |
| CTGATGCATC | TGCTAATATG | TCAAGAATTG | TAACTTACTC | AGATTTTGG | TGGAAAGGTA | 4380 |
| AATTAGTATT | TAAAGCTAAA | CTAAGAGCCT | CTCATACTTG | GAATCCAATT | CAACAAATGA | 4440 |
| GTATTAATGT | AGATAACCAA | TTTAACTATG | TACCAAGTAA | TATTGGAGGT | ATGAAAATTG | 4500 |

-continued

| | | | | | | |
|---|---|---|---|---|---|---|
| TATATGAAAA | ATCTCAACTA | GCACCTAGAA | AATTATATTA | ACATACTTAC | TATGTTTTTA | 4560 |
| TGTTTATTAC | ATATCAACTA | GCACCTAGAA | AATTATATTA | ATATACTTAC | TATGTTTTTA | 4620 |
| TGTTTATTAC | ATATTATTTT | AAGATTAATT | AAATTACAGC | ATAGAAATAT | TGTACTTGTA | 4680 |
| TTTGATATAG | GATTTAGAAG | GTTTGTTATA | TGGTATACAA | TAACTGTAAG | AAATAGAAGA | 4740 |
| ACATCTAGAT | CATAGTTAGT | AGTTTGTTTT | ATAAATGTA | TTGTAAACCA | TTAATGTATG | 4800 |
| TTGTTATGGT | GTGGGTGGTT | GGTTGGTTTG | CCCTTAGAAT | ATGTTAAGGA | CCAAAAAAAA | 4860 |
| TCAATAAAAG | ACATTTAAAA | TTAAATGGCC | TCGTATACTG | TCTATAAGGT | GAACTAACCT | 4920 |
| TACCATAAGT | ATCAATCTGT | CTTTAAGGGG | GGGGTGGGTG | GGAGATGCAC | AACATCAGTA | 4980 |
| GACTGACTGG | CCTGGTTGGT | TGCTCTGCTT | AATCAACCAG | ACCGCGTAGC | GGTCTGGTTG | 5040 |
| ATTAAGCGC | | | | | | 5049 |

( 2 ) INFORMATION FOR SEQ ID NO:2:

( i ) SEQUENCE CHARACTERISTICS:
        ( A ) LENGTH: 5049 base pairs
        ( B ) TYPE: nucleic acid
        ( C ) STRANDEDNESS: both
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Parvovirus ( x i ) SEQUENCE DESCRIPTION: SEQ ID NO:2:

| | | | | | | |
|---|---|---|---|---|---|---|
| ATCATTCTTT | AGAACCAACT | GACCAAGTTC | ACGTACGTAT | GACGTGATGA | CGCGCGCTGC | 60 |
| GCGCGCTGCC | TACGGCAGTC | ACACGTCATA | CGTACGCTCC | TTGGTCAGTT | GGTTCTAAAG | 120 |
| AATGATAGGC | GGTTTGTGTG | TTTAAACTTG | GGCGGGAAAA | GGTGGCGGGC | TAATTGTGGG | 180 |
| CGTGGTTAAA | GGTATAAAAG | ACAAACCATA | GACCGTTACT | GACATTCGCT | TCTTGTCTTT | 240 |
| GACAGAGTGA | ACCTCTCTTA | CTTTGACTAA | CCATGTCTGG | CAACCAGTAT | ACTGAGGAAG | 300 |
| TTATGGAGGG | AGTAAATTGG | TTAAAGAAAC | ATGCAGAAAA | TGAAGCATTT | TCGTTTGTTT | 360 |
| TTAAATGTGA | CAACGTCCAA | CTAAATGGAA | AGGATGTTCG | CTGGAACAAC | TATACCAAAC | 420 |
| CAATTCAAAA | TGAAGAGCTA | ACATCTTTAA | TTAGAGGAGC | ACAAACAGCA | ATGGATCAAA | 480 |
| CCGAAGAAGA | AGAAATGGAC | TGGGAATCGG | AAGTTGATAG | TCTCGCCAAA | AAGCAAGTAC | 540 |
| AAACTTTTGA | TGCATTAATT | AAAAAATGTC | TTTTTGAAGT | CTTTGTTTCT | AAAAATATAG | 600 |
| AACCAAATGA | ATGTGTTTGG | TTTATTCAAC | ATGAATGGGG | AAAAGATCAA | GGCTGGCATT | 660 |
| GTCATGTTTT | ACTTCATAGT | AAGAACTTAC | AACAAGCAAC | TGGTAAATGG | CTACGCAGAC | 720 |
| AAATGAATAT | GTATTGGAGT | AGATGGTTGG | TGACTCTTTG | TTCGGTAAAC | TTAACACCAA | 780 |
| CTGAAAAGAT | TAAGCTCAGA | GAAATTGCAG | AAGATAGTGA | ATGGGTGACT | ATATTAACAT | 840 |
| ACAGACATAA | GCAAACAAAA | AAAGACTATG | TTAAAATGGT | TCATTTTGGA | AATATGATAG | 900 |
| CATATTACTT | TTTAACAAAG | AAAAAAATTG | TCCACATGAC | AAAAGAAAGT | GGCTATTTTT | 960 |
| TAAGTACTGA | TTCTGGTTGG | AAATTTAACT | TTATGAAGTA | TCAAGACAGA | CAAATTGTCA | 1020 |
| GCACACTTTA | CACTGAACAA | ATGAAACCAG | AAACCGTTGA | AACCACAGTG | ACGACAGCAC | 1080 |
| AGGAAACAAA | GCGCGGGAGA | ATTCAAACTA | AAAAGGAAGT | GTCAATCAAA | TGTACTTTGC | 1140 |
| GGGACTTGGT | TAGTAAAAGA | GTAACATCAC | CTGAAGACTG | GATGATGTTA | CAACCAGATA | 1200 |

```
GTTATATTGA  AATGATGGCA  CAACCAGGAG  GTGAAAATCT  TTTAAAAAAT  ACACTTGAAA   1260

TTTGTACTTT  GACTTTAGCA  AGAACAAAAA  CAGCATTTGA  ATTAATACTT  GAAAAGCAG    1320

ATAATACTAA  ACTAACTAAC  TTTGATCTTG  CAAATTCTAG  AACATGTCAA  ATTTTTAGAA   1380

TGCACGGATG  GAATTGGATT  AAAGTTTGTC  ACGCTATAGC  ATGTGTTTTA  AATAGACAAG   1440

GTGGTAAAAG  AAATACAGTT  CTTTTCATG   GACCAGCAAG  TACAGGAAAA  TCTATCATTG   1500

CTCAAGCCAT  AGCACAAGCT  GTGGGTAATG  TTGGTTGTTA  TAATGCAGCA  AATGTAAATT   1560

TTCCATTTAA  TGACTGTACC  AATAAAAATT  TAATTTGGAT  TGAAGAAGCT  GGTAACTTTG   1620

GTCAACAAGT  TAATCAATTT  AAAGCAATCT  GTTCTGGACA  AACAATTAGA  ATTGATCAAA   1680

AAGGTAAAGG  AAGTAAGCAA  ATTGAACCAA  CTCCAGTAAT  TATGACAACT  AATGAAAATA   1740

TAACAATTGT  GAGAATTGGA  TGTGAAGAAA  GACCTGAACA  TACACAACCA  ATAAGAGACA   1800

GAATGTTGAA  CATTAAGTTA  GTATGTAAGC  TTCCAGGAGA  CTTTGGTTTG  GTTGATAAAG   1860

AAGAATGGCC  TTTAATATGT  GCATGGTTAG  TTAAACATGG  TTTTGAATCA  ACCATGGCTA   1920

ACTATACACA  TCATTGGGGA  AAAGTACCAG  AATGGGATGA  AAACTGGGCG  GAGCCTAAAA   1980

TACAAGAAGG  TATAAATTCA  CCAGGTTGCA  AAGACTTAGA  GACACAAGCG  GCAAGCAATC   2040

CTCAGAGTCA  AGACCAAGTT  CTAACTCCTC  TGACTCCGGA  CGTAGTGGAC  CTTGCACTGG   2100

AACCGTGGAG  TACTCCAGAT  ACGCCTATTG  CAGAAACTGC  AAATCAACAA  TCAAACCAAC   2160

TTGGCGTTAC  TCACAAAGAC  GTGCAAGCGA  GTCCGACGTG  GTCCGAAATA  GAGGCAGACC   2220

TGAGAGCCAT  CTTTACTTCT  GAACAATTGG  AAGAAGATTT  TCGAGACGAC  TTGGATTAAG   2280

GTACGATGGC  ACCTCCGGCA  AAGAGAGCCA  GGAGAGGTAA  GGGTGTGTTA  GTAAAGTGGG   2340

GGGAGGGGAA  AGATTTAATA  ACTTAACTAA  GTATGTGTTT  TTTTATAGGA  CTTGTGCCTC   2400

CAGGTTATAA  ATATCTTGGG  CCTGGGAACA  GTCTTGACCA  AGGAGAACCA  ACTAACCCTT   2460

CTGACGCCGC  TGCAAAAGAA  CACGACGAAG  CTTACGCTGC  TTATCTTCGC  TCTGGTAAAA   2520

ACCCATACTT  ATATTTCTCG  CCAGCAGATC  AACGCTTTAT  AGATCAAACT  AAGGACGCTA   2580

AAGATTGGGG  GGGGAAAATA  GGACATTATT  TTTTTAGAGC  TAAAAGGCA   ATTGCTCCAG   2640

TATTAACTGA  TACACCAGAT  CATCCATCAA  CATCAAGACC  AACAAAACCA  ACTAAAGAA    2700

GTAAACCACC  ACCTCATATT  TTCATCAATC  TTGCAAAAAA  AAAAAAAGCC  GGTGCAGGAC   2760

AAGTAAAAAG  AGACAATCTT  GCACCAATGA  GTGATGGAGC  AGTTCAACCA  GACGGTGGTC   2820

AACCTGCTGT  CAGAAATGAA  AGAGCTACAG  GATCTGGGAA  CGGGTCTGGA  GGCGGGGGTG   2880

GTGGTGGTTC  TGGGGGTGTG  GGGATTTCTA  CGGGTACTTT  CAATAATCAG  ACGGAATTTA   2940

AATTTTTGGA  AAACGGATGG  GTGGAAATCA  CAGCAAACTC  AAGCAGACTT  GTACATTTAA   3000

ATATGCCAGA  AAGTGAAAAT  TATAGAAGAG  TGGTTGTAAA  TAATTTGGAT  AAAACTGCAG   3060

TTAACGAAAA  CATGGCTTTA  GATGATACTC  ATGCACAAAT  TGTAACACCT  TGGTCATTGG   3120

TTGATGCAAA  TGCTTGGGGA  GTTTGGTTTA  ATCCAGGAGA  TTGGCAACTA  ATTGTTAATA   3180

CTATGAGTGA  GTTGCATTTA  GTTAGTTTTG  AACAAGAAAT  TTTTAATGTT  GTTTTAAAGA   3240

CTGTTTCAGA  ATCTGCTACT  CAGCCACCAA  CTAAAGTTTA  TAATAATGAT  TTAACTGCAT   3300

CATTGATGGT  TGCATTAGAT  AGTAATAATA  CTATGCCATT  TACTCCAGCA  GCTATGAGAT   3360

CTGAGACATT  GGGTTTTTAT  CCATGGAAAC  CAACCATACC  AACTCCATGG  AGATATTATT   3420

TTCAATGGGA  TAGAACATTA  ATACCATCTC  ATACTGGAAC  TAGTGGCACA  CCAACAAATA   3480

TATACCATGG  TACAGATCCA  GATGATGTTC  AATTTTATAC  TATTGAAAAT  TCTGTGCCAG   3540

TACACTTACT  AAGAACAGGT  GATGAATTTG  CTACAGGAAC  ATTTTTTTTT  GATTGTAAAC   3600
```

-continued

```
CATGTAGACT  AACACATACA  TGGCAAACAA  ATAGAGCATT  GGGCTTACCA  CCATTTCTAA   3660
ATTCTTTGCC  TCAATCTGAA  GGAGGTACTA  ACTTTGGTTA  TATAGGAGTT  CAACAAGATA   3720
AAAGACGTGG  TGTAACTCAA  ATGGGAAATA  CAAACTATAT  TACTGAAGCT  ACTATTATGA   3780
GACCAGCTGA  GGTTGGTTAT  AGTGCACCAT  ATTATTCTTT  TGAGGCGTCT  ACACAAGGGC   3840
CATTTAAAAC  ACCTATTGCA  GCAGGACGGG  GGGGAGCGCA  AACAGATGAA  AATCAAGCAG   3900
CAGATGGTGA  TCCAAGATAT  GCATTTGGTA  GACAACATGG  TCAAAAAACT  ACCACAACAG   3960
GAGAAACACC  TGAGAGATTT  ACATATATAG  CACATCAAGA  TACAGGAAGA  TATCCAGAAG   4020
GAGATTGGAT  TCAAAATATT  AACTTTAACC  TTCCTGTAAC  AGATGATAAT  GTATTGCTAC   4080
CAACAGATCC  AATTGGAGGT  AAAACAGGAA  TTAACTATAC  TAATATATTT  AATACTTATG   4140
GTCCTTTAAC  TGCATTAAAT  AATGTACCAC  CAGTTTATCC  AAATGGTCAA  ATTTGGGATA   4200
AAGAATTTGA  TACTGACTTA  AAACCAAGAC  TTCATGTAAA  TGCACCATTT  GTTTGTCAAA   4260
ATAATTGTCC  TGGTCAATTA  TTTGTAAAAG  TTGCGCCTAA  TTTAACAAAT  GAATATGATC   4320
CTGATGCATC  TGCTAATATG  TCAAGAATTG  TAACTTACTC  AGATTTTGG   TGGAAGGTA    4380
AATTAGTATT  TAAAGCTAAA  CTAAGAGCCT  CTCATACTTG  GAATCCAATT  CAACAAATGA   4440
GTATTAATGT  AGATAACCAA  TTTAACTATG  TACCAAGTAA  TATTGGAGGT  ATGAAAATTG   4500
TATATGAAAA  ATCTCAACTA  GCACCTAGAA  AATTATATTA  ACATACTTAC  TATGTTTTTA   4560
TGTTTATTAC  ATATCAACTA  GCACCTAGAA  AATTATATTA  ATATACTTAC  TATGTTTTTA   4620
TGTTTATTAC  ATATTATTTT  AAGATTAATT  AAATTACAGC  ATAGAAATAT  TGTACTTGTA   4680
TTTGATATAG  GATTTAGAAG  GTTTGTTATA  TGGTATACAA  TAACTGTAAG  AAATAGAAGA   4740
ACATTTAGAT  CATAGTTAGT  AGTTTGTTTT  ATAAAATGTA  TTGTAAACCA  TTAATGTATG   4800
TTGTTATGGT  GTGGGTGGTT  GGTTGGTTTG  CCCTTAGAAT  ATGTTAAGGA  CCAAAAAAAA   4860
TCAATAAAAG  ACATTTAAAA  CTAAATGGCC  TCGTATACTG  TCTATAAGGT  GAACTAACCT   4920
TACCATAAGT  ATCAATCTGT  CTTTAAGGGG  GGGGTGGGTG  GGAGATGCAC  AACATCAGTA   4980
GACTGACTGG  CCTGGTTGGT  TGCTCTGCTT  AATCAACCAG  ACCGCGTAGC  GGTCTGGTTG   5040
ATTAAGCGC                                                                5049
```

ATTENUATED CANINE PARVOVIRUS VACCINE

1. INTRODUCTION

The invention is directed to a novel attenuated canine parvovirus (CPV) strain which may be used as a veterinary vaccine against CPV disease. The invention is further directed to a virus stock generated from a genomic DNA clone of such attenuated CPV virus for use as a veterinary vaccine, and methods for its production.

2. BACKGROUND OF THE INVENTION

During 1978 and 1979, outbreaks of previously unrecognized disease were observed in dogs in a number of countries. Identification of the causative agent, canine parvovirus (CPV), was made when comparisons between the disease seen in dogs and those caused in cats by feline panleukopenia virus (FPV) or in minks by mink enteritis virus (MEV), both parvoviruses, were noted. CPV has become endemic in domestic and wild dog populations around the world. Rapid global spread of the virus was most likely due to the high viral titers found in feces of infected dogs (Parrish, C. R., Adv. Virus Res. 38:403–450, 1990).

Two clinical conditions are recognized—enteric disease in dogs older than 4 to 5 months, and myocardial disease in pups 3 to 16 weeks old. CPV is responsible for serious illness and mortality in dogs, and pups less than 6 months old are particularly susceptible (Carmichael et al., Cornell Vet. 73:13–29, 1983).

Canine parvovirus (CPV) is an autonomous parvovirus with a DNA genome of about 5,000 bases of single-stranded DNA. Two structural genes are characterized (VP-1 and VP-2), as well as one or two non-structural (NS) genes (Parrish et al. J. Virol, 65:6544–6552, 1991).

The original strain of CPV (CPV-2), first identified in 1978, was almost completely replaced between 1979 and 1982 by an antigenic and genetic variant, CPV-2a. A later antigenic variant, CPV-2b, emerged around 1984 and became the predominant virus type by 1988. It has largely replaced the previous strains in the United States, such that over 90% of infected dogs now carry this strain. DNA sequence analysis shows that sequence variation in the VP1/VP2 genes gave rise to successive antigenic virus types, such that the CPV-2a strain differed in only 5 or 6 amino acids from CPV-2, while CPV-2b differs in only 2 amino acids from CPV-2a (Parrish et al. J. Virol 65:6544–6552, 1991).

Vaccines designed to elicit protection against previous strains of CPV have been developed, including live (U.S. Pat. No. 4,303,645 dated Dec. 1, 1981; U.S. Pat. No. 4,810,494 dated Mar. 7, 1989) inactivated (U.S. Pat. No. 4,193,991 dated Mar. 18, 1980), heterotypic (U.S. Pat. No. 4,193,990 dated Mar. 18, 1980) as well as recombinant subunit vaccines (U.S. Pat. No. 4,971,793 dated Nov. 20, 1990; Lopez de Turiso et al., J. Virol. 66:2748–2753, 1992). Baculovirus expression of the CPV capsid genes generated empty parvoviral capsids which could be used to immunize dogs against challenge with CPV-2b (Mazzara et al., Vaccines '87, Cold Spring Harbor Laboratory Press, 1987, p. 419–424; Saliki et al., J. Gen. Virol. 73:369–374, 1992).

The advantage of a vaccine derived from an attenuated virus over a heterotypic, inactivated, or recombinant vaccine is that the virus is able to reproduce in the host system such that an immune response is maintained over time.

No attenuated vaccines have yet been developed which are derived from the most recent CPV-2b strain that is the most prevalent form of the virus found in infected dogs.

3. SUMMARY OF THE INVENTION

It is an object of the present invention to provide attenuated canine parvoviruses derived from serial passaging of a virulent CPV-2b isolate. Such viruses are provided herein, the DNA of which differs in nucleotide sequence from that of wild-type CPV-2b. The DNA from the attenuated strains is used for the production of infectious molecular DNA clones, which, in turn, can be transfected into cells to generate stable master stocks of the virus. The attenuated viruses can be used in dogs as a vaccine for the prevention of CPV disease. In a preferred embodiment, the attenuated virus vBI440 (ATCC Deposit No. VR 2489) is used as the vaccine.

4. DESCRIPTION OF THE FIGURES

FIG. 3A–3C represents the DNA sequence of CPV-39 passage #60 which was cloned into pBI440.

FIG. 4A–4C represents the DNA sequence of CPV-39 passage #5.

5. DETAILED DESCRIPTION OF THE INVENTION

Figure 1:
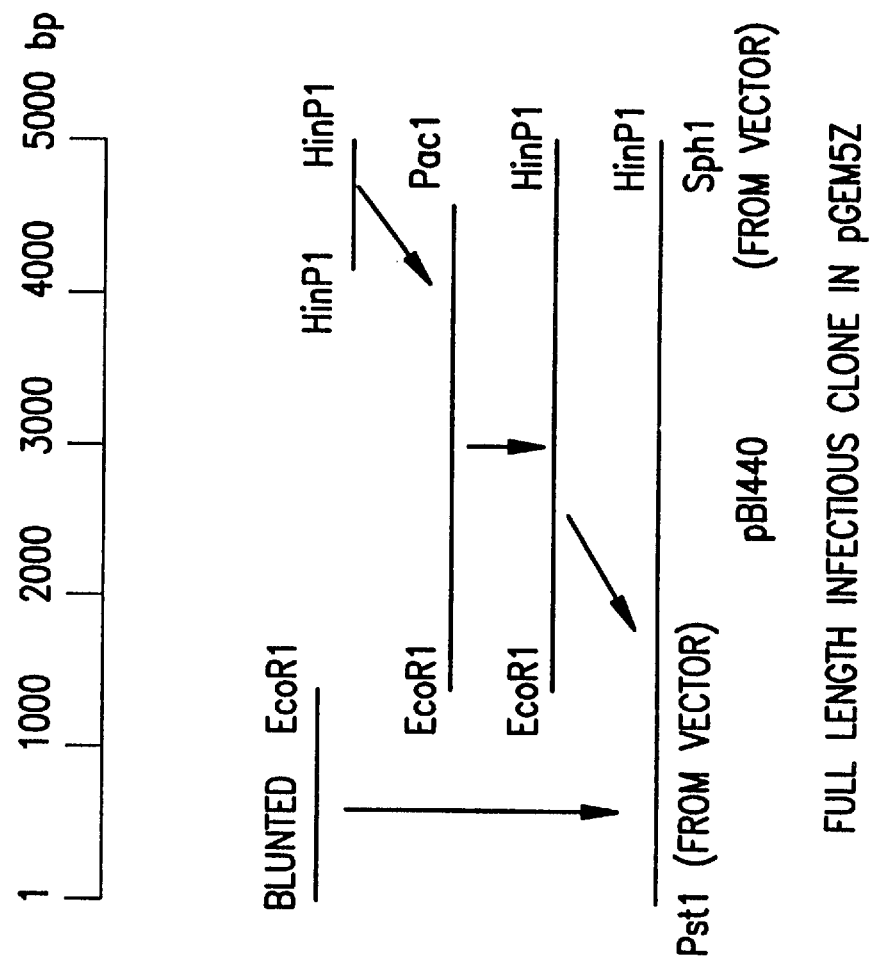
FIG. 1 represents a schematic diagram of the full-length CPV genome and the subcloned fragments of the genome which were ligated to form a continuous fragment that was cloned into plasmid pGEM5Z.

In one embodiment of the invention, a novel attenuated strain of canine parvovirus useful as a veterinary vaccine against CPV disease has been isolated. An infectious molecular DNA clone based on the genome of the attenuated strain has been produced and it may be used to generate a stable master stock of the attenuated CPV strain.

5.1. Isolation of Attenuated Canine Parvovirus

This embodiment of the present invention is directed to the isolation of an attenuated strain of canine parvovirus as a vaccine to protect animals, such as wild or domestic dogs, against CPV. Attenuation of a virulent isolate of CPV is achieved by serial passaging of such virus in a suitable host cell line (see e.g., Carmichael et al., Cornell Vet. 71:408–471, 1981) over time so that mutations accumulate that confer attenuation on the isolate. Serial passaging refers to the infection of a cell line with a virus isolate, the recovery of the viral progeny from the host cells, and the subsequent infection of host cells with the viral progeny to generate the next passage. Cell lines for the passaging of CPV include Norden Laboratory feline kidney (NLFK), mink lung cells, Madin-Darby canine kidney cells, canine A72 cells, and Crandell feline kidney (CRFK) cells.

Virulent CPV may be recovered from the feces of infected dogs and subsequently grown in tissue culture cells (Appel et al., Vet. Rec. 105:156–159, 1979). Isolation of CPV may be performed by disruption of infected cells with sonication or cycles of freezing and thawing followed by virus purification (Parrish, Virology 183:195–205, 1991).

CPV isolates which may be used to develop an attenuated strain that is protective against CPV-2b include, but is not limited to, CPV-39 as well as other isolates known to those skilled in the art (Parrish et al., J. Virol. 65:6544–6552, 1991).

Serial passaging of a virulent (disease-causing) strain of CPV results in the isolation of variants which are attenuated, i.e., infectious, yet not capable of causing disease. These attenuated variants are identified through testing of a passaged isolate on a suitable subject population, i.e., dogs, so that the clinical profile of the infected subjects can be ascertained. When a passaged virus is identified that infects dogs, yet is incapable of causing disease, it is characterized as attenuated. This passaged virus is then further characterized for its ability to serve as a vaccine against CPV disease, i.e., to confer protective immunity against challenge with virulent CPV.

In one embodiment of the invention, a virulent CPV-2b isolate was serially passaged in NLFK cells to derive the attenuated strain. Serial passaging was performed by infecting NLFK cells with the virulent strain, incubating the infected cells for several days, collecting and then freezing and thawing the infected cells to release virus. An inoculum from the previous passage was then applied to fresh, thinly seeded NLFK cells to generate the next passage. Each passage was similarly performed and collected. Hemagglutination (HA) assay of selected passages was used to identify the endpoint dilution of virus, and this dilution was used to generate the next passage.

In an embodiment of the invention described, infra, various passages in the series were tested for clinical effect. Dogs from 8–35 weeks of age were inoculated with passaged virus, either by oro-nasal or subcutaneous routes. The virulence of a passaged virus, i.e., the ability to cause disease, was assessed by daily monitoring of reduced appetite, malaise, elevated temperature, vomiting/diarrhea, lymphopenia, weight loss and fecal shed in the infected dogs. Virulence was retained up to the 15th passage, while attenuation was observed at subsequent passages. The 60th passage was attenuated, as judged by the inability of this virus to elicit clinical signs of CPV disease (Table 1, infra) (Abstract presented at the Fifth Parvovirus Workshop, Crystal River, Fla., Nov. 10–14, 1993.) Serial backpassages of this strain in dogs did not cause reversion to virulence.

5.2. Construction of an Infectious CPV Clone from an Attenuated Strain and the Generation of an Attenuated Stock The DNA genome of autonomous parvoviruses is able to initiate a productive infection when introduced into host cells by transfection. The infectious DNA genome of an attenuated virus is engineered into a vector for introduction into host cells for the production of progeny virus which are genetically identical to the parent attenuated isolate. The vector may be engineered to carry the viral genome using standard in vitro recombinant DNA techniques known to those skilled in the art (Ausubel et al., Current Protocols in Molecular Biology, Greene Publishing Associates & Wiley Interscience, New York, 1989). Vectors which may be used to deliver the genome into host cells include pGEM3Z, pGEM5Z (Promega Corporation, Madison, Wis.), and other similar plasmid vectors. Stable master stocks of a virus with desirable characteristics, i.e., attenuation, may be generated.

The ability to generate viral progeny through plasmid-mediated introduction of a viral genome can also be used to produce viruses with defined molecular changes. In this embodiment of the invention, stable virus stocks can be produced that contain altered DNA sequences that confer desired properties on the virus, for example, reduced virulence. This approach can also be used to assess the effect of molecular changes on various properties of the virus, i.e., antigenic type, virulence, or attenuation by introducing desired sequence changes into the viral genome, producing virus progeny from the genome, and recovering the virus progeny for characterization. In addition, this approach can be used to construct a virus with heterologous sequences inserted into the viral genome that are concurrently delivered by the virus to generate an immune response against other diseases. Such diseases include, but are not limited to, canine adenovirus, canine distemper virus, canine corona virus, and Leptospira.

Construction of viral genomes with defined molecular changes can be accomplished using standard techniques such as oligonucleotide-directed, linker-scanning or polymerase chain reaction-based mutagenesis techniques known to those skilled in the art (Zoller and Smith DNA 3:479–488, 1984; Botstein and Shortle Science 229:1193, 1985; Ausubel et al., Current Protocols in Molecular Biology, Greene Publishing Associates & Wiley Interscience, New York, 1989, Chapter 8). Ligation of the genome into a suitable vector for transfer may be accomplished through standard techniques known to those skilled in the art. Transfection of the vector into host cells for the production of viral progeny may be done using any of the standard techniques such as calcium-phosphate or DEAE-dextran mediated transfection, electroporation, protoplast fusion, and other techniques known to those skilled in the art (Sambrook et al., Molecular Cloning: A Laboratory Manual, Cold Spring Harbor Laboratory Press, 1989).

In one embodiment of the present invention, viral DNA was prepared from the attenuated strain derived from the 60th passage of CPV-2b and cloned into a plasmid for transfer into host cells by transfection. Progeny virus was produced and recovered from the transfected cells. The resulting virus stock (vBI440) was confirmed as an attenuated strain. This virus was used as a vaccine against virulent CPV-2b.

5.3. Sequence of Attenuated Canine Parvovirus

The isolation of an attenuated virus may be followed by a sequence analysis of its genome to determine the basis for the attenuated phenotype. This is accomplished by sequencing the viral DNA and identifying nucleotide changes in the attenuated isolate relative to the genomic sequence of a control virus. Therefore, the molecular changes that confer attenuation on a virulent strain can be characterized.

In an embodiment of the invention, the sequence of the DNA genome isolated from the attenuated virus (60th passage) was determined and compared to a control genome (5th passage). Nucleotide sequence variations between the virulent strain and the attenuated strain were identified. Four nucleotide alterations were found in the attenuated virus genome, in the 5' and 3' nontranslated regions (Table 2).

The invention provides for attenuated CPV-2b viruses which have one or more of the following sequence alterations relative to the sequence of the control (5th passage) wild-type CPV-2b (SEQ. ID NO. 2):

| | |
|---|---|
| nucleotide at position 59 | A or C or T |
| nucleotide at position 97 | A or G or T |
| nucleotide at position 4745 | A or G or C |
| nucleotide at position 4881 | A or G or T |

In one embodiment of the invention provided herein, the viral genome with alterations at all 4 positions (SEQ. ID. NO. 1) relative to the wild-type sequence was used to produce an attenuated virus stock. Other embodiments include the introduction of sequence changes at 1, 2 or 3 of the sites noted above in order to generate attenuated virus progeny. Viral genomes with such alterations can be produced by any of the techniques described in Section 5.2, supra, for the introduction of nucleotide changes into cloned DNA. A genome may then be ligated into an appropriate vector for transfection into host cells (Section 5.2, infra) for the production of viral progeny.

5.4. Attenuated Canine Parvovirus as a Vaccine

The invention may be used as a vaccine to protect dogs from disease resulting from challenge with all extant strains of CPV, types 2, 2a and 2b. The vaccine may be an attenuated virus isolate, or, alternatively, the vaccine may be comprised of virus which has been generated from an infectious genomic clone of an attenuated virus.

Preparation of the vaccine may be accomplished by growing large-scale stocks of the attenuated virus in tissue culture. Alternatively, the plasmid which contains the genome of the attenuated virus may be transfected into host cells to generate large-scale virus stock. The viruses may be recovered from host cells by disruption by, for example, sonication or cycles of freezing and thawing (Parrish, Virology 183:195–205, 1991).

Determination of virus yield may be performed with the use of a hemagglutination assay (Carmichael et al., Am. J. Vet. Res. 41: 784–791, 1980) or plaque assay (Chang et al., J. Virol. 66:6858–6867, 1988).

The vaccine may be comprised of an inoculum which is an aliquot from an attenuated virus stock. The vaccine may be prepared as a suspension or, alternatively, the vaccine may be lyophilized. The attenuated virus may be suspended in a pharmaceutically acceptable carrier, including but not limited to, phosphate-buffered saline.

The attenuated virus may be combined with other ingredients and antigens for the production of a vaccine. The attenuated virus may be given in combination with other antigens, including, but not limited to, canine adenovirus, canine distemper virus, canine coronavirus, or Leptospira antigens to form a combination vaccine. Stabilizers may be added to such a vaccine, including but not limited to, gelatin, sorbitol, mannitol, glucose, sucrose, dextran, albumin, SPGA (Bovarnick, J. Bact. 59:509, 1950) or others known to those skilled in the art.

Subject populations for evaluation of a candidate vaccine include wild and domestic dogs.

Dosage of the vaccine may range from about $10^2$ to about $10^7$ tissue culture infectious dose$_{50}$ (TCID$_{50}$). A dosage greater than $10^7$ TCID$_{50}$ may be given. In a preferred embodiment, the dosage is $10^5$ TCID$_{50}$. A minimal immunizing dose (MID) may be determined by vaccinating a subject population with graded 10-fold dilutions of an attenuated virus stock, and assaying the animals for HI titer (Carmichael et al., Cornell Vet. 73:13–29, 1983).

The vaccine may be administered by several parenteral routes, including subcutaneously, intramuscularly, or intravenously. Repeated administration may be given, including but not limited to, yearly booster shots.

The safety of the vaccine can be determined by the absence of adverse effects, i.e., evidence of illness generated by the administration of the vaccine in a test population prior to challenge with virulent virus.

The immune response generated by the vaccine can be assayed by testing sera from inoculated dogs using hemagglutination-inhibition (HI) titers (Carmichael et al., Am. J. Vet. Res. 41: 784–791, 1980). The development of antibodies to the attenuated virus correlates with an increase in HI titer, and the generation of this protective response is defined as vaccination. Protection can be correlated with the development of an HI titer that exceeds 1:40.

The efficacy of the vaccine can be determined by the ability of the vaccine to confer resistance on a subject population when challenged with virulent CPV. Challenge may performed when an interval has elapsed after vaccination, for example, from 14–20 days. Duration of immunity afforded by the vaccine may be determined by periodic assessment of HI titers in vaccinated animals or by challenge with virulent CPV and observation of clinical signs of CPV disease.

In one embodiment of the invention, virus derived from the infectious molecular clone of the attenuated strain (vBI440) was used to vaccinate pups (Section 9, infra). After challenge with virulent CPV, the vaccinated dogs did not evidence signs of disease. Hemagglutination-inhibition (HI) titers of the vaccinated animals showed the development of a serological response to the attenuated virus vaccine.

6. EXAMPLE: ISOLATION OF ATTENUATED CANINE PARVOVIRUS STRAIN

6.1. Methods

To produce a virus strain capable of eliciting protection against virulent CPV-2b, a CPV-2b isolate (CPV-39) was obtained from the Texas Veterinary Medical Diagnostic Laboratory (accession number C84176071, No. 2). This isolate was confirmed as a CPV-2b isolate by typing against a panel of monoclonal antibodies (Parrish et al., J. Virol. 65:6544–6552, 1991). The virus was originally passaged five times in NLFK cells to establish a stock virus preparation.

The NLFK host cells used in these experiments were grown in a mixture of 50% McCoy's 5a and 50% Leibovitz L15 media with 5% fetal bovine serum at 37° C.

CPV-39 was serially passaged in NLFK cells. Serial passaging was performed by infecting NLFK cells with CPV-39, incubating the infected cells for between 5–7 days, and then freezing and thawing the infected cells to release viral progeny. Virus from the cell lysate (1–2 ml) was then applied to fresh, thinly seeded NLFK cells to generate the subsequent passage in the series. Each passage was similarly performed and collected.

At various passages (pass 3, 15, 20, 25, 35, 44, 50 and 60) the virus-containing materials were diluted in a 10-fold series in tissue culture medium, and the dilutions inoculated onto thinly seeded NLFK cells. After incubation for 4–5 days, the cultures were frozen and thawed, and the medium tested for virus hemagglutination of rhesus macaque erythrocytes (HA assay). The subsequent passage in each case was made using the culture inoculated with the endpoint dilution of the virus as determined in the HA assay.

The HA assay was performed in a microtiter plate by incubating 0.025 ml of a virus dilution per well with 0.025 ml of barbitol-buffered saline (BBS) to which is added 0.050 ml of a 0.5% v/v suspension of rhesus erythrocytes in BBS/bovine serum albumin (BSA). The plate was shaken to mix and placed at 4° C. for the cells to settle. The HA titer is read as the last well containing >50% agglutinated cells.

Various passages in the series were tested for the ability to induce disease in dogs. In each test between 2 and specific-pathogen-free (SPF) beagle dogs, aged between 8–35 weeks, were inoculated with $10^{5.5}$ to $10^{6.5}$ tissue culture infectious dose-50 ($TCID_{50}$) units of passaged virus, either by oro-nasal (ON) or subcutaneous (SC) routes. Virulence was judged by reduced appetite, malaise, elevated temperature, vomiting/diarrhea and weight loss, while attenuation was judged by the reduction or absence of these symptoms within 10 days post-infection.

6.2. Results

Virulence was retained up to the 15th passage (#15), was greatly reduced by the 20th passage (#20), while the 60th 25 passage (#60) caused no clinical symptoms in susceptible puppies (Table 1), and was characterized as attenuated. Non-inoculated control dogs remained clinically normal.

7. EXAMPLE: PRODUCTION OF VIRUS FROM MOLECULAR CLONE OF ATTENUATED STRAIN

7.1. Methods

Stock virus was prepared from the 60th passage by infecting thinly seeded NLFK cells. After culturing the virus-infected cells for 36 hours, the cells were lysed and the viral replicative form (RF) DNA (double-stranded) was recovered using a modification of the Hirt procedure for the isolation of low molecular weight DNA (Parrish et al., Amer. J. Vet. Res. 45:2591–2599, 1984). The recovered DNA was purified by preparative agarose gel electrophoresis (Ausubel et al., Current Protocols in Molecular Biology, Greene Publishing Associates & Wiley Interscience, New York, 1989), and the viral RF DNA was recovered from the gel by electroelution (Ausubel et al., supra).

The viral DNA genome was subcloned as shown in FIG. 1 by restriction and assembled into a single continuous sequence, then ligated into plasmid pGEM5Z to derive plasmid pBI440. 10 µg of this plasmid was electroporated into NLFK cells (at 220V/330 uF) to initiate a virus infection from the genome.

Virus generated by the transfection of the infectious genomic clone was recovered from the NLFK cells by freezing and thawing. The resulting virus (vBI440) was tested against a panel of type-specific monoclonal antibodies by hemagglutination-inhibition (HI) assay (see Section 9, infra) and the derivation of this virus from the original CPV-39 was confirmed (Parrish et al., J. Virol. 65: 6544–6552, 1991).

Eight 9 week-old beagle pups were inoculated subcutaneously with $10^{5.5}$ to $10^{6.5}$ tissue culture infectious dose-50 ($TCID_{50}$) units of the vBI440 strain to determine if the attenuated phenotype of the parent virus (#60 passage) was retained.

7.2. Results

Clinical analysis of the pups inoculated with vBI440 (#60-cloned strain) revealed that this virus did not cause any signs of CPV disease (Table 1), as judged by the absence of CPV-like symptoms, and therefore could be characterized as attenuated. Serial backpassages of this strain in dogs did not cause illness.

The virus derived from passage #60 in the series was passaged for another 15 passages in NLFK cells, at which time a non-hemagglutinating variant emerged. In contrast, 15 passages of vBI440 in NLFK cells showed no apparent phenotypic variation, illustrating the stability of the virus derived from the genome of the attenuated strain.

TABLE 1

Clinical Responses of Pups Inoculated by the Oral-Nasal (On) or Subcutaneous (Sc) Route with Different Passage Levels of CPV-2b and Infectious Clone of Passage #60

| Virus Passage | No. Dogs/age/ Route Inoc. | Reduced Appetite | Malaise | Elevated Temp[1] | Vomiting/ Diarrhea | Lympho- penia[2] | Weight Loss[3] | Fecal Shed[4] |
|---|---|---|---|---|---|---|---|---|
| #3 | 5/20 wk/)N | 5/5 | 5/5 | 4/5 | 5/5 | 5/5 | 5/5 | 5/5 |
| #15 | 3/17 wk/ON | 2/3 | 0/3 | 1/3 | 0/3 | 3/3 | 3/3 | 3/3 |
| #20 | 2/16 wk/ON | 0/2 | 0/2 | 1/2 | 0/2 | 2/2 | 0/2 | 2/2 |
| #25 | 2/8 wk/SC | 0/2 | 0/2 | 1/2 | 0/2 | 2/2 | 0/2 | 2/2 |
| " | 2/8 wk/ON | 1/2 | 0/2 | 2/2 | 0/2 | 2/2 | 0/2 | 2/2 |
| #35 | 2/10 wk/SC | 1/2 | 1/2 | 1/2 | 1/2 | 2/2 | 2/2 | 2/2 |
| #44 | 5/35 wk/SC | 0/5 | 0/5 | 4/5 | 0/5 | Not Done | 0/5 | 5/5 |
| #50 | 2/8 wk/ON | 0/2 | 0/2 | 0/2 | 0/2 | 2/2 | 0/2 | 2/2 |
| " | 2/8 wk/SC | 0/2 | 0/2 | 0/2 | 0/2 | 2/2 | 0/2 | 2/2 |
| #60 | 5/8 wk/SC | 0/5 | 0/5 | 0/5 | 0/5 | 2/5 (2 day) | 0/5 | 2/2 |
| #60 - cloned virus | 8/9 wk/SC | 0/8 | 0/8 | 1/8 (1 day) | 0/8 | 0/8 | 0/8 | 0/8 |

[1]Number of dogs/total inoculated at this passage with temperature $\geq 103°$ F.
[2]Lymphopenia = lymphocyte counts <50% of pre-inoculation value. Total WBC counts done by Coulter counter. No dog had a panleukopenia.
[3]Weight loss = failure to gain normal weight or actual weight loss between time of infection and 2 weeks later.
[4]Fecal hemagglutination titer >2048 for at least 2 days.

8. EXAMPLE: SEQUENCE ANALYSIS OF CLONED ATTENUATED VIRUS

8.1. Methods

Plasmid pBI440, containing the viral DNA of passage #60 cloned into pGEM5Z, was subcloned into M13 phage vectors mp18 and mp19 and the DNA was sequenced by the dideoxy method (Ausubel et al., Current Protocols in Molecular Biology, Greene Publishing Associates & Wiley Interscience, New York, (1989) using primers as described previously (Parrish et al., 1991, Virology 183:195–205). DNA prepared from the CPV-39 5th passage (#5) was also cloned into pGEM5Z and pGEM3Z and sequenced as a comparative control.

8.2. Results

Figure 2:
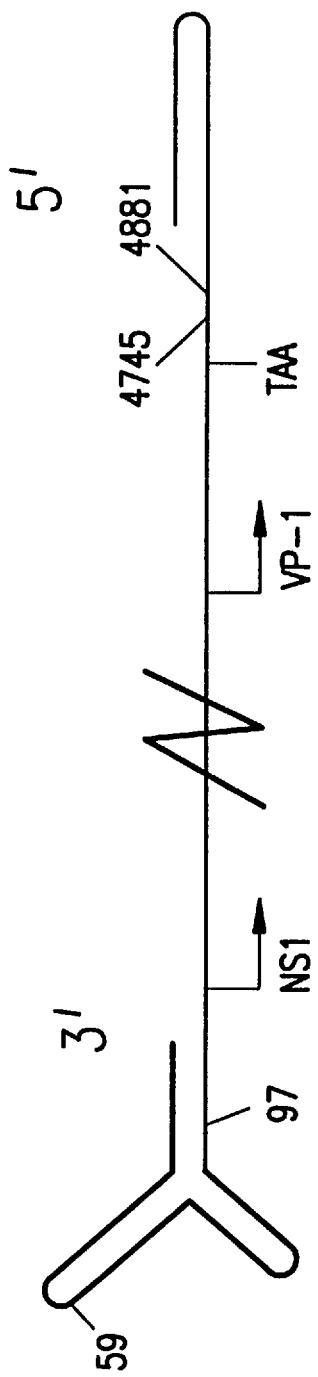
FIG. 2 represents a schematic diagram of the positions of the sequence changes detected in pBI440 relative to the control genome of the #5 passage, showing the 5' and 3' changes relative to coding regions and secondary structures in the CPV genome.

The sequence of the attenuated virus genome derived from passage #60 is given in FIG. 3A–3C (SEQ. ID. NO. 1). The sequence of the control virus used for sequence comparison (passage #5) is given in FIG. 4A–4C (SEQ. ID. NO. 2). Comparative differences between these genomes are shown in Table 2. Nucleotide changes at 4 positions in pBI440 (passage #60) relative to that observed in the control plasmid (passage #5) were identified. Two changes at the 5' end, at positions 4745 and 4881, occurred in the non-coding region. At the 3' end, nucleotide changes at positions 59 and 97 were also in the non-coding region, and within the hairpin potentially formed by the palindromic sequence at that terminus (FIG. 2).

TABLE 2

SEQUENCE VARIATION IN ATTENUATED CPV-2b

| Nucleotide | Passage 5 | Passage 60 |
|---|---|---|
| 59 | G | A |
| 97 | C or T | T |
| 4745 | T | C |
| 4881 | C | T |

9. EXAMPLE: VACCINATION WITH ATTENUATED vBI440

9.1. Methods

Five SPF 12.5 week-old beagle pups were vaccinated by the subcutaneous route with 1 dose ($10^5$ TCID$_{50}$/ml) of vBI440. Two control pups were kept in isolation until challenge with virulent CPV-39. Challenge was performed at 20 days after vaccination and consisted of inoculation with $10^{6.2}$ TCID$_{50}$ units in 3 ml of inoculum.

Pre-inoculation blood samples were taken for leukocyte counts and at intervals for 8 days post-challenge. Dogs were observed twice daily for signs of illness, including rectal temperatures. Fecal samples were also collected during the same time period and pooled samples from each isolation unit were prepared as a 10% volume suspension in phosphate-buffered saline and then tested for virulent viral shed using an HA assay.

Blood for serological testing was obtained on post-vaccination days 0, 7 and 21 and 10 days after challenge with virulent CPV-2b. Hemagglutination-inhibition (HI) titers of the vaccinated animals were performed by collecting animal sera and diluting 1:5 in BBS, then heat inactivating at 56° C. for 30 minutes. To the sera, 0.010 ml 50% packed red blood cells were added, and the mixture was allowed to stand for 1 hour at 4° C. In a microtiter well, 0.025 ml BBS, and serial dilutions of heat-inactivated sera, beginning at 0.025 ml, were added, followed by 0.025 ml of diluted antigen. Incubation of the plates for 1 hour at room temperature was followed by the addition of 0.050 ml 0.5% RBC suspension. An antigen control was set up by setting up a parallel plate without sera. All plates were shook and placed at 4° C. for 4–16 hours. The HI titer is the reciprocal of the highest serum dilution that completely prevents hemagglutination.

9.2. Results

The vaccine, vBI440, did not cause symptoms of illness, as indicated by the normal temperature observed in vaccinated animals 1411–1415 (Table 3A, column days post-inoculation (DPI): −1, 0) as well as normal leukocyte values (Table 3A, column DPI: 0).

For 9 days following challenge with virulent CPV-39, all vaccinated animals (1411–1415) maintained normal temperature and normal blood values (WBC and Ly/PMN) (Table 3A, column DPI: 1–9). Fecal HA titers indicated no shed of virulent virus in the vaccinated animals. The vaccination with vBI440 offered protection against challenge with CPV-39, while non-vaccinated animals were susceptible to challenge.

In contrast, the non-vaccinated animals (1418, 1419) showed elevated temperatures by day 5 in the course of a 9-day period post-challenge, as well as a marked lymphopenia on days 4–7 (Table 3B, column Ly/PMN: 4-7) and leukopenia on day 6 (column WBC: 6). Fecal shed of virulent virus was observed on days 4 and 5, as determined from an HA assay.

The vaccine vBI440 elicited serological protection for the 5 vaccinated pups challenged with virulent CPV-39, as evidenced by the HI antibody titers in Table 4A. For vaccinated animals 1411–1415, HI titers had increased by 1 week post-vaccination relative to pre-inoculation levels (Table 4A, 1 wk. PI), further increasing by 3 weeks post-vaccination (Table 4A, 3 wk. PI), indicating that the antibodies to vBI440 had developed which afforded protection against the subsequent challenge with CPV-39. In contrast, in non-vaccinated animals 1418 and 1419, no significant HI titers were detected prior to challenge (Table 4B, prechallenge). Following challenge, non-vaccinated animals evidenced the development of antibodies to CPV after the course of disease had abated, as indicated by the increased HI titers observed at 10 and 21 days post-challenge (Table 4B).

TABLE 3

CLINICAL RESPONSES TO VACCINATION WITH vBI440 AND CHALLENGE WITH VIRULENT CPV-2b

A. DOG NUMBER (v = vaccinated)

| DPI | 1411-V Temp WBC[1]/Ly/PMN | 1412-V Temp WBC/Ly/PMN | 1413-V Temp WBC/Ly/PMN | 1414-V Temp WBC/Ly/PMN | 1415-V Temp WBC/Ly/PMN |
|---|---|---|---|---|---|
| −1 | 102.0 . . . | 102.3 . . . | 102.5 . . . | 102.6 . . . | 102.3 . . . |
| 0 | 101.2 8.1/46/54 | 101.2 7.2./51/49 | 100.9 10.2/47/53 | 102.5 11.1/49/51 | 101.3 9.2/45/55 |
| 1 | 101.3 . . . | 101.8 . . . | 102.4 . . . | 101.8 . . . | 100.9 . . . |
| 2 | 102.4 9.0/40/60 | 102.5 8.0/46/54 | 101.7 9.2/44/56 | 100.8 10.7/45/55 | 102.2 10.0/50/50 |
| 3 | 102.0 7.7/39/61 | 102.4 7.6/40/60 | 102.0 9.9/49/51 | 102.8 9.7/47/53 | 101.8 9.5/39/51 |
| 4 | 102.2 . . . | 102.4 | 102.1 . . . | 102.4 . . . | 102.0 . . . |
| 5 | 102.3 8.7/47/53 | 101.9 7.9/36/64 | 101.3 11.3/35/65 | 102.7 10.2/40/60 | 102.2 9.0/42/58 |

TABLE 3-continued

CLINICAL RESPONSES TO VACCINATION WITH vBI440 AND CHALLENGE WITH VIRULENT CPV-2b

| 6 | 101.8 9.4/44/66 | 101.8 8.7/39/61 | 102.0 11.0/39/61 | 102.3 11.3/37/63 | 101.8 9.8/41/59 |
| 7 | 101.5 . . . | 101.6 . . . | 101.5 . . . | 101.7 . . . | 101.9 . . . |
| 8 | 101.1 10.7/45/55 | 101.8 9.5/41/59 | 101.6 10.3/45/55 | 102.2 11.2/40/60 | 101.7 10.2/47/53 |
| 9 | 101.8 . . . | 101.9 . . . | 101.9 . . . | 102.7 . . . | 102.2 . . . |

FECAL HA: Titers were all less than 1:32 (generally 1:8–1:16) before and after challenge, indicating no shed of virulent (challenge) virus.

B. SPF controls challenged with CPV-2b (passage 5):

| | 1418-c | | | 1419-c | | |
| --- | --- | --- | --- | --- | --- | --- |
| Post-challenge day | Temp | WBC/Ly/PMN | Weight | Temp. | WBC/Ly/PMN | Weight | Fecal HA (Pool) |
| 0 | 102.6 | 11.0/42/59 | 12.3# | 102.4 | 9.8/36/64 | 12# | 1:32 |
| 1 | 101.8 | . . . | | 101.3 | . . . | | 1:16 |
| 2 | 102.8 | 10.9/55/65 | | 103.0 | 9.5/41/59 | | 1:16 |
| 3 | 102.0 | . . . | | 102.6 | . . . | | 1:512 |
| 4 | 101.8 | 8.1/7/93 | | 103.1 | 8.9/10/90 | | 1:65,536 |
| 5 | 102.6 | 9.2/9/91 | | 102.4 | 9.0/7/93 | | 1:162,144 |
| 6 | 103.0 | 4.4/40/60 | | 102.6 | 4.5/38/62 | | no feces |
| 7 | 102.2 | . . . | | 103.2 | . . . | | 1:64 |
| 8 | 101.5 | . . . | 10.6# | 102.0 | . . . | 10.2# | 1:64 |
| 9 | 101.8 | 8.9/47/53 | | 101.9 | 8.5/40/60 | | 1:16 |
| 10 | 101.4 | . . . | | 101.7 | . . . | | 1:16 |

TABLE 4

SEROLOGICAL RESPONSES TO VACCINATION WITH vBI440

A. HI Antibody Titers (CPV-2b antigen):

| | 1411 | 1412 | 1413 | 1414 | 1415 |
| --- | --- | --- | --- | --- | --- |
| Pre-inoc. | <10 | <10 | <10 | <10 | <10 |
| 1 wk. P1 | 2560 | 5120 | 1280 | 2560 | 2560 |
| 3 wk. P1 (pre-challenge) | 5120 | 10,240 | 5120 | 10,240 | 10,240 |
| 10 days post-challenge | 5120 | 10,240 | 2560 | 2560 | 2560 |

B. Serology (HI antibody titer):

| | 1418-C | 1419-C |
| --- | --- | --- |
| Prechallenge: | <10 | <10 |
| 10 days | 5120 | 5120 |
| 21 days | 10,240 | 5120 |

10. DEPOSIT OF MICROORGANISMS

The following microorganisms were deposited with the American type Culture Collection (ATCC), Rockville, Md., on Oct. 28, 1994, and have been assigned the following accession numbers:

| Virus | Accession Numbers |
| --- | --- |
| CPV-39 passage #60 | ATCC No. VR 2491 |
| vBI440 | ATCC No. VR 2489 |
| CPV-39 passage #5 | ATCC No. VR 2490 |

| Plasmid | |
| --- | --- |
| pBI440 | ATCC No. 75938 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosure of which are incorporated by reference in their entireties.

We claim:

1. A DNA molecule encoding an attenuated canine parvovirus genome, comprising the nucleotide sequence as depicted in SEQ. ID. NO. 1.

2. A DNA molecule encoding a canine parvovirus genome, comprising the nucleotide sequence as depicted in SEQ. ID. NO. 2, wherein position #59 is A, C, or T.

3. A DNA molecule encoding a canine parvovirus genome, comprising the nucleotide sequence as depicted in SEQ. ID. NO. 2, wherein position #97 is A, G, or T.

4. A DNA molecule encoding a canine parvovirus genome, comprising the nucleotide sequence as depicted in SEQ. ID. NO. 2, wherein position #i4745 is A, G, or C.

5. A DNA molecule encoding a canine parvovirus genome, comprising the nucleotide sequence as depicted in SEQ. ID. NO. 2, wherein position #4881 is A, G, or T.

6. The DNA molecule of claim 2, in which position #97 is A, G, or T, which DNA molecule encodes an attenuated canine parvovirus genome.

7. The DNA molecule of claim 2, in which position #4745 is A, G, or C, which DNA molecule encodes an attenuated canine Parvovirus genome.

8. The DNA molecule of claim 2 in which position #4881 is A, G, or T, which DNA molecule encodes an attenuated canine parvovirus genome.

9. The DNA molecule of claim 3, in which position #4745 is A, G, or C. which DNA molecule encodes an attenuated canine parvovirus genome.

10. The DNA molecule of claim 4, in which position #4881 is A, G, or T, which DNA molecule encodes an attenuated canine parvovirus genome.

11. The DNA molecule of claim 4, in which position #4881 is A, G, or T, which DNA molecule encodes an attenuated canine parvovirus genome.

12. The DNA molecule of claim 6, in which position #4745 is A, G, or C, which DNA molecule encodes an attenuated canine parvovirus genome.

13. The DNA molecule of claim 6, in which position #4881 is A, G, or T, which DNA molecule encodes an attenuated canine parvovirus genome.

14. The DNA molecule of claim 7, in which position #4881 is A, G, or T, which DNA molecule encodes an attenuated canine parvovirus genome.

15. The DNA molecule of claim 9, in which position #4881 is A, G, or T, which DNA molecule encodes an attenuated canine parvovirus genome.

16. The DNA molecule of claim 12, in which position #4881 is A, G, or T, which DNA molecule encodes an attenuated canine parvovirus genome.

17. The virus derived from the 60th passage of CPV-39, deposited as ATCC Deposit No. VR 2491.

18. The virus vBI440, deposited as ATCC Deposit No. VR 2489.

19. The plasmid pBI440, deposited as ATCC Deposit No. 75938.

20. A virus containing a genome consisting of the DNA molecule of claim 2, 3, 4, 5, 6, 7, 8, 9, 10, 11, 12, 13, 14, 15 or 16.

21. A vaccine, comprising the virus of claim 19, and a pharmaceutically acceptable carrier.

22. A vaccine, comprising the virus of claim 20, and a pharmaceutically acceptable carrier.

23. A vaccine, comprising the virus of claim 22, and a pharmaceutically acceptable carrier.

24. A method of protecting an animal from canine parvovirus disease comprising inoculating the animal with an effective amount of the vaccine of claim 21.

25. A method of protecting an animal from canine parvovirus disease comprising inoculating the animal with an effective amount of the vaccine of claim 22.

26. The method of claim 24 or 25 in which the vaccine is administered by an intramuscular, intradermal, intravenous, or subcutaneous route.

27. The method of claim 24 or 25 in which the vaccine is administered at a dose from about $10^2$ TCID$_{50}$ to about $10^7$ TCID$_{50}$.

28. The method of claim 24 or 25 in which the vaccine is administered at a dose greater than about $10^7$ TCID$_{50}$.

29. The method of claim 24 or 25 in which the animals are wild or domestic dogs.

30. A method for producing an attenuated type 2b canine parvovirus vaccine, comprising cloning the DNA molecule of claim 1, 6, 7, 8, 9, 10, 11, 12, 13, 14, 15 or 16 into a vector, transfecting the vector into a host cell, producing progeny attenuated type 2b canine parvovirus in the transfected host cell, and recovering the attenuated type 2b canine parvovirus vaccine.

31. The method of claim 30, in which the vector is pGEM3Z or pGEM5Z.

32. The method of claim 30 in which the host cell is selected from the group consisting of Norden Laboratory feline kidney cells, mink lung cells, Madin-Darby canine kidney cells, or canine A72 cells.

33. A method for producing a type 2b canine parovovirus immunogenic composition, comprising cloning the DNA molecule of claim 2, 3, 4 or 5 into a vector, transfecting the vector into the host cell, producing progeny type 2b canine parvovirus in the transfected host cell, and recovering the type 2b canine parovirus vaccine.

* * * * *

UNITED STATES PATENT AND TRADEMARK OFFICE
CERTIFICATE OF CORRECTION

PATENT NO. : 5,814,510

DATED : September 29, 1998

INVENTOR(S) : Parrish et al.

It is certified that error appears in the above-identified patent and that said Letters Patent is hereby corrected as shown below:

Claim 4, column 21, line 56, "i4745" should read "4745".

Claim 10, column 22, line 47, "claim 4" should read "claim 3".

Claim 21, column 23, line 10, "claim 19" should read "claim 17".

Claim 22, column 23, line 12, "claim 20" should read "claim 18".

Claim 23, column 23, line 14, "claim 22" should read "claim 20".

Claim 31, column 24, line 13, should read as follows: The method of claim 30 in which the DNA is derived from vBI440.

Claim 32, column 24, line 15, should read as follows: The method of claim 30 in which the vector is pGEM3Z or pGEM5Z.

Claim 33, column 24, line 19, should read as follows: The method of claim 30 in which the host cell is selected from the group consisting of Norden Laboratory feline kidney cells, mink lung cells, Madin-Darby canine kidney cells, and canine A72 cells.

Claim 34, column 24, line 25, should read as follows: A method for producing a type 2b canine parvovirus immunologic composition, comprising cloning the DNA molecule of claim 2, 3, 4, or 5 into a vector, transfecting the vector into a host cell, producing progeny type 2b canine parvovirus in the transfected host cell, and recovering the type 2b canine parvovirus immunologic composition.

Signed and Sealed this

Thirty-first Day of August, 1999

Attest:

Q. TODD DICKINSON

*Attesting Officer*       *Acting Commissioner of Patents and Trademarks*